United States Patent
Ogino et al.

(10) Patent No.: US 8,580,312 B2
(45) Date of Patent: Nov. 12, 2013

(54) RADIATION THERAPY AGENT

(75) Inventors: Chiaki Ogino, Kobe (JP); Tsutomu Tanaka, Kobe (JP); Ryohei Sasaki, Kobe (JP); Akihiko Kondo, Kobe (JP)

(73) Assignee: National University Corporation Kobe University, Hyogo (JP)

( * ) Notice: Subject to any disclaimer, the term of this patent is extended or adjusted under 35 U.S.C. 154(b) by 0 days.

(21) Appl. No.: 13/578,836

(22) PCT Filed: Feb. 17, 2011

(86) PCT No.: PCT/JP2011/053348
§ 371 (c)(1),
(2), (4) Date: Sep. 11, 2012

(87) PCT Pub. No.: WO2011/102407
PCT Pub. Date: Aug. 25, 2011

(65) Prior Publication Data
US 2013/0017266 A1    Jan. 17, 2013

(30) Foreign Application Priority Data

Feb. 17, 2010   (JP) ................................ 2010-032055

(51) Int. Cl.
A61P 35/00   (2006.01)
A61K 9/14    (2006.01)
A61K 39/395  (2006.01)
C07K 16/18   (2006.01)
C07K 16/00   (2006.01)

(52) U.S. Cl.
USPC ........ 424/490; 424/178.1; 428/402; 977/773; 977/911

(58) Field of Classification Search
None
See application file for complete search history.

(56) References Cited

U.S. PATENT DOCUMENTS

| 5,045,318 A | 9/1991 | Tengvall et al. |
| 2006/0281087 A1 | 12/2006 | Sonezaki et al. |
| 2008/0207440 A1* | 8/2008 | Tucker .......................... 502/350 |
| 2009/0130050 A1 | 5/2009 | Kanehira et al. |
| 2009/0297620 A1 | 12/2009 | Kanehira et al. |

FOREIGN PATENT DOCUMENTS

| JP | 2-503001 | 9/1990 |
| JP | 10-328316 | 12/1998 |
| JP | 2008-156158 | 7/2008 |
| JP | 2008-156167 | 7/2008 |
| JP | 2008-195653 | 8/2008 |
| JP | 2008-201797 | 9/2008 |
| WO | 2004-087765 A1 | 10/2004 |
| WO | 2009-144775 A1 | 12/2009 |

OTHER PUBLICATIONS

Liu et al., "Monitor of X-ray Activation of TiO2 nanoparticles for CT26 Cells Therapy by SR-FTIR", 2007, 14A1 BM—IR Microscopy, p. 11-146.*
Cai et al., "Induction of Cytotoxicity by Photoexcited TiO2 Particles," Cancer Research, No. 52, Apr. 15, 1992, pp. 2346-2348 (4 pages).
Zhang et al., "Photocatalytic killing effect of TiO2 nanoparticles on Ls-174-t human colon carcinoma cells," World Journal of Gastroenterology, No. 10 (21), 2004, pp. 3191-3193 (3 pages).
Liu et al., "Sonodynamic effects of protoporphyrin IX disodium salt on isolated sarcoma 180 cells," Ultrasonics, No. 45, 2006, pp. 56-60 (5 pages).
Honda et al., "Effects of Dissolved Gases and an Echo Contrast Agent on Apoptosis Induced by Ultrasound and Its Mechanism Via the Mitochondria-Caspase Pathway," Ultrasound in Medicine & Biology, vol. 28, No. 5, 2002, pp. 673-682 (10 pages).
Matsui et al., Abstracts of Annual Meeting of the Society of Chemical Engineers, Japan, Feb. 18, 2009, vol. 74 p. S413 (in Japanese) (2 pages).
Matsui et al., "Antibody-immobilized TiO2 nanoparticles for cancer therapy," Abstracts, Journal of Bioscience and Bioengineering, BM-P15, vol. 108, Issue S1, 2009, pp. S36-S37 (3 pages).
Ichinose, 2-3, Kasanka Titanium, Hikari Shokubai Seihin Kanri Sekininsha Koshu Kanri Sekininsha Koshu Text, Hikari Shokubai Seihin Gijutsu Kyogikai, Apr. 3, 2005 (in Japanese) (8 pages).
Karasaki et al., Abstracts of the Annual Meeting of the Society for Biotechnology, Japan, Sep. 25, 2010, vol. 62, p. 168 (in Japanese).
International Search Report issued in corresponding International Patent Application No. PCT/JP2011/053348 mailed Mar. 22, 2011 (4 pages).

* cited by examiner

Primary Examiner — Robert A Wax
Assistant Examiner — Randeep Singh
(74) Attorney, Agent, or Firm — Kilyk & Bowersox, P.L.L.C.

(57) ABSTRACT

Provided is a radiotherapeutic agent, including a composite particle, which is obtained by binding a molecule that specifically recognizes a target to a substrate particle including titanium peroxide, and which generates reactive oxygen through irradiation with a radiation. Further, because the radiotherapeutic agent contains the molecule that specifically recognizes a target, the radiotherapeutic agent has a function of accumulating in the target. The radiotherapeutic agent is capable of enhancing effects of radiotherapy, and is capable of reducing side effects on a living body to efficiently attack the target.

11 Claims, 4 Drawing Sheets

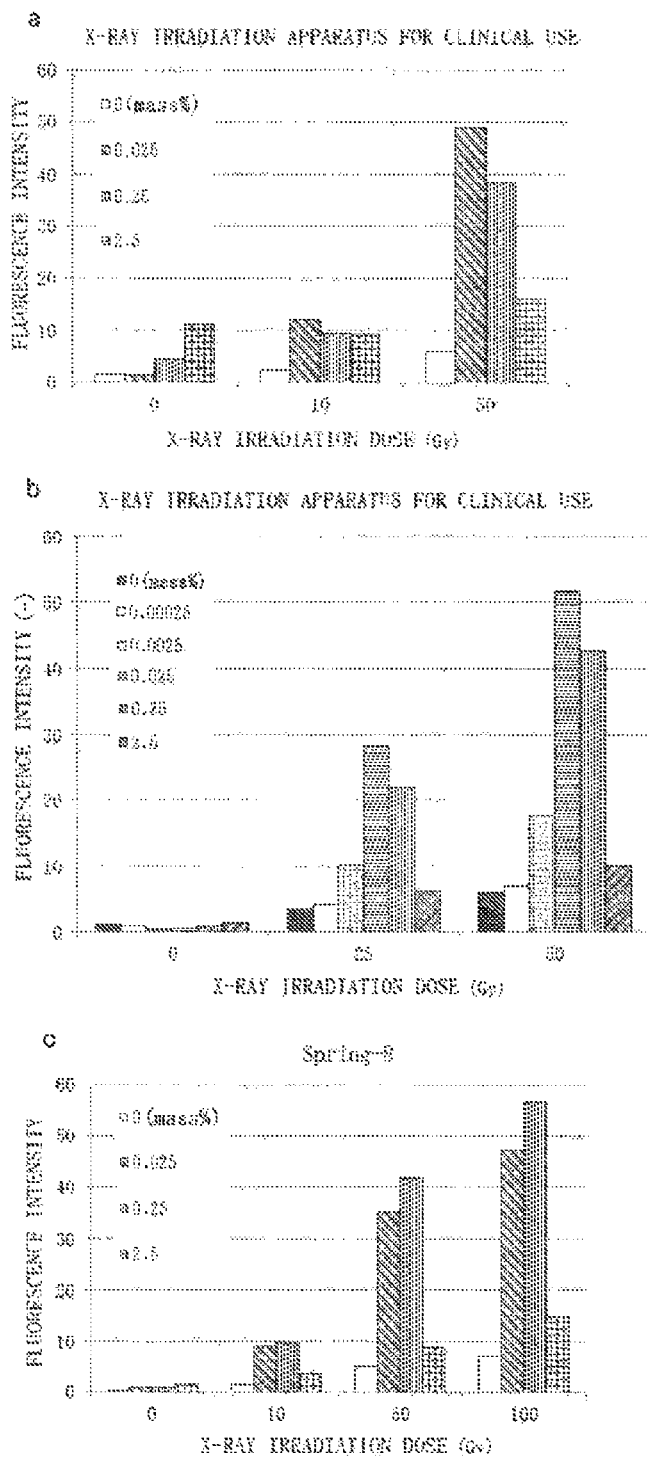

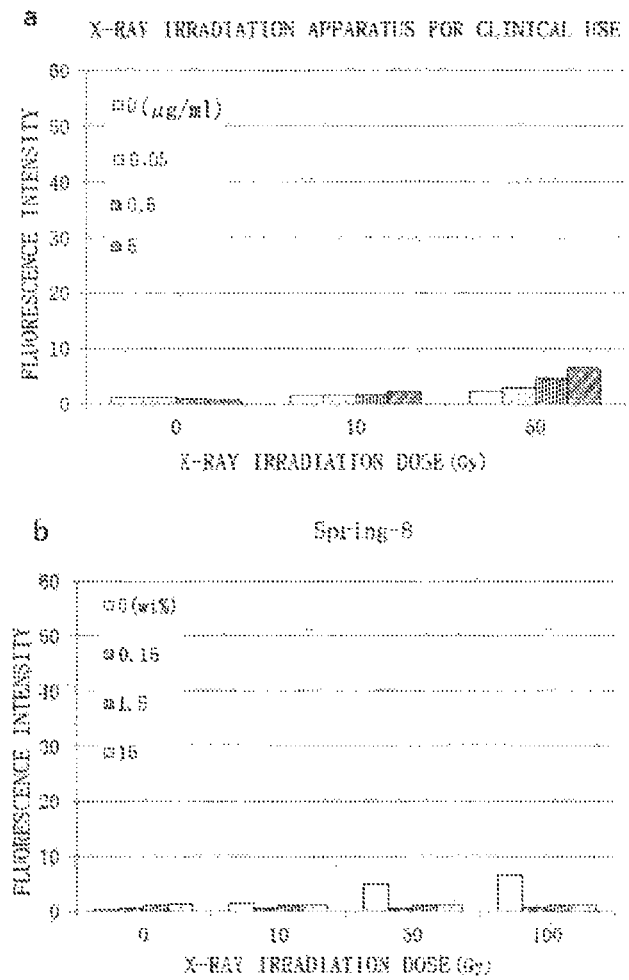
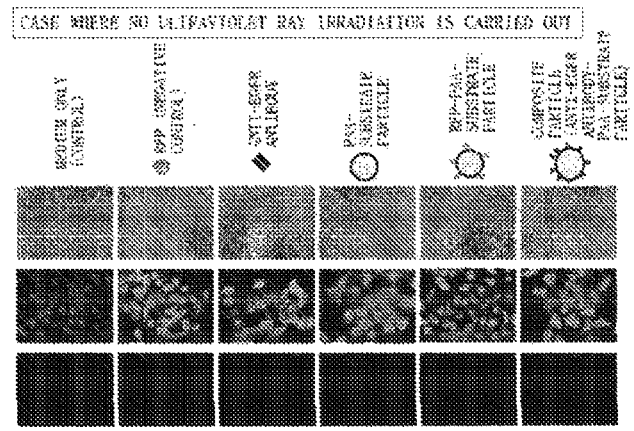

RADIATION THERAPY AGENT

TECHNICAL FIELD

The present invention relates to a radiotherapeutic agent, including a composite particle obtained by binding a molecule that specifically recognizes a target to a substrate particle containing titanium peroxide, in which the composite particle generates a hydroxyl radical through radiation irradiation.

The present application is a National Stage Application of PCT/JP2011/053348, filed Feb. 17, 2011, which claims priority from Japanese Patent Application No. 2010-032055, which is incorporated herein by reference.

BACKGROUND ART

Radiotherapy is carried out as one of the therapies for cancer. The radiotherapy is a therapy involving suppressing growth of cancer cells and killing cancer cells through irradiation with an X-ray, a γ-ray, or the like. The radiotherapy is considered to be an important measure for palliative medicine, because it is generally a local therapy, is less invasive to the whole body, and hence allows a burden on a patient to be reduced.

In the radiotherapy, an external irradiation method is a method involving irradiating a focus as a target from the outside of the body, and uses an X-ray, a γ-ray, an electron beam, a particle beam, or the like. In the external irradiation method, it is necessary to consider a direction of radiation irradiation so that a sufficient dose of radiation reaches a tumor and a normal tissue around the tumor does not receive a high dose of radiation. Radiation irradiation may be carried out from one direction, or may be carried out from numerous directions. A therapy for a tumor present in a deep portion in the body requires strong radiation irradiation, which causes problems in terms of side effects.

The side effects of the radiotherapy on a normal tissue basically occur in an irradiated region. A response of the normal tissue is exemplified by mucosal or epithelial cell damage, which develops during irradiation, and interstitial cell or vascular endothelial cell damage, which develops six months to several years after completion of the therapy. The radiotherapy causes various side effects depending on an irradiation dose, an irradiation site, a patient's age and systemic condition, and the like. There is a demand for radiotherapy capable of effectively killing cancer cells while reducing the side effects.

In recent years, a photocatalytic action of titanium dioxide or the like has been utilized in various fields and has attracted attention. The photocatalytic action is based on an oxidizing ability of a reactive oxygen species to be generated by irradiating titanium dioxide or the like with light having a short wavelength of 380 nm or less. The photocatalytic action has been utilized in a decomposition treatment of hazardous chemical substances such as an environmental hormone and in killing and suppressing growth of hazardous microorganisms, and further, its applied research toward the therapies for cancer is proceeding (Non Patent Literatures 1 to 4).

It has been disclosed that a titanium dioxide composite, which is obtained by modifying titanium dioxide with a hydrophilic polymer and further immobilizing thereto a molecule having a specific binding ability to a molecule of interest, has an action of decomposing cancer cells and the like through a photocatalytic action (Patent Literature 1). Such titanium dioxide composite exerts a photocatalytic action through ultraviolet ray irradiation.

Further, it has been confirmed that titanium dioxide generates a hydroxyl radical at a high concentration when subjected to ultrasonic irradiation (titanium dioxide/sonocatalytic method). There is a disclosure of a composite particle obtained by coating titanium dioxide with polyacrylic acid and binding a liver cell recognition protein pre/S2 to the titanium dioxide. Such composite particle is capable of specifically targeting liver cancer cells and exerts actions of killing/damaging cancer cells through ultrasonic irradiation (Patent Literature 2).

Although it has been demanded that the photocatalytic action be utilized in the radiotherapy, no photocatalytic material which can be put into practical use has been found yet, because there are problems in terms of an irradiation dose and the like.

CITATION LIST

Patent Literature

[PTL 1] WO 2004/087765 A1
[PTL 2] JP 2008-195653 A

Non Patent Literature

[NPL 1] R, Cai, Y. Kubota, T. Shuin, et al., Cancer Res. 52 (1992) 2346-2348.
[NPL 2] World J Gastroenterol 10 (2004) 3191-3193.
[NPL 3] Q. Liu, X. Wang, P. Wang, et al., Ultrasonics 2006; 45: 56-60.
[NPL 4] H. Honda, Q. L. Zhao, T. Kondo., Ultrasound in Med. & Biol. 28 (2002) 673-682.

SUMMARY OF INVENTION

Technical Problem

An object of the present invention is to provide a radiotherapeutic agent, including a particle which generates a hydroxyl radical through radiation irradiation.

Solution to Problem

In order to achieve the object, the inventors of the present invention have made extensive studies. As a result, the inventors have focused attention on the generation of a hydroxyl radical from titanium peroxide through radiation irradiation, and have found that titanium peroxide can be used in radiotherapy. Thus, the present invention has been completed.

That is, the present invention includes the following items.
1. A radiotherapeutic agent, including a composite particle, which is obtained by binding a molecule that specifically recognizes a target to a substrate particle including titanium peroxide, and which generates reactive oxygen that damages the target through irradiation with a radiation.
2. A radiotherapeutic agent according to the item 1, in which the reactive oxygen includes a hydroxyl radical.
3. A radiotherapeutic agent according to the item 1 or 2, in which the titanium peroxide in the substrate particle is mainly distributed on a surface of the substrate particle.
4. A radiotherapeutic agent according to any one of the items 1 to 3, in which the substrate particle further includes titanium dioxide.
5. A radiotherapeutic agent according to any one of the items 1 to 4, in which the substrate particle has an average dispersed particle diameter of 1 nm or more to 200 nm or less.

6. A radiotherapeutic agent according to any one of the items 1 to 5, in which the molecule that specifically recognizes a target includes an antibody.

7. A radiotherapeutic agent according to any one of the items 1 to 6, in which the composite particle includes the substrate particle whose surface is at least partially coated with a polymer coating film, and is obtained by binding the molecule that specifically recognizes a target to the substrate particle via the polymer coating film.

8. A radiotherapeutic agent according to any one of the items 1 to 7, in which the radiation includes an X-ray.

9. A dispersion liquid, including a composite particle self-dispersed in water, a pH buffer, an infusion liquid, or physiological saline, in which the composite particle includes a composite particle, which is obtained by binding a molecule that specifically recognizes a target to a substrate particle including titanium peroxide, and which generates reactive oxygen that damages the target through irradiation with a radiation.

10. A dispersion liquid according to the item 9, in which the composite particle has a surface potential of +20 mV or more.

11. A radiotherapeutic agent, including the dispersion liquid according to the item 9 or 10.

12. An antitumor agent, including the radiotherapeutic agent according to any one of the items 1 to 8 and 11, in which the molecule that specifically recognizes a target includes an antibody capable of specifically recognizing a tumor cell.

Advantageous Effects of Invention

According to the radiotherapeutic agent of the present invention, a composite particle is accumulated in a target through a molecule that specifically recognizes the target, and titanium peroxide generates a hydroxyl radical through radiation irradiation, which allows the target to be damaged. The use of the radiotherapeutic agent of the present invention allows the target to be effectively damaged even at a small radiation dose. When the radiotherapeutic agent of the present invention is used to carry out oncotherapy or the like, side effects of a radiation on a normal tissue other than a tumor can be reduced. Further, if a high therapeutic effect is achieved at a small dose, the burden of radiotherapy on a patient is reduced and the usefulness of radiotherapy is increased. In the conventional radiotherapy, limitations are imposed on an irradiation dose, irradiation frequency, and the like from the viewpoints of side effects and the like. However, the use of the radiotherapeutic agent of the present invention in combination is expected to provide a sufficient therapeutic effect even in the conventional range.

BRIEF DESCRIPTION OF DRAWINGS

FIGS. 3a, 3b, and 3c Graphs each showing the amount of a hydroxyl radical generated in the case where a titanium peroxide-titanium dioxide substrate particle is irradiated with an X-ray through the use of an X-ray irradiation apparatus for clinical use (FIGS. 3a and 3b) or Spring-8 (FIG. 3c) (Experimental Example 1).

FIGS. 4a and 4b Graphs each showing the amount of a hydroxyl radical generated in the case where a polyacrylic acid (PAA)-modified titanium dioxide fine particle is irradiated with an X-ray through the use of an X-ray irradiation apparatus for clinical use (FIG. 4a) or Spring-8 (FIG. 4b) (Experimental Example 1).

FIG. 5 Photographs each showing cytotoxicity in the case where a composite particle of the present invention is not irradiated with an ultraviolet ray (Experimental Example 2).

DESCRIPTION OF EMBODIMENTS

Figure 1:
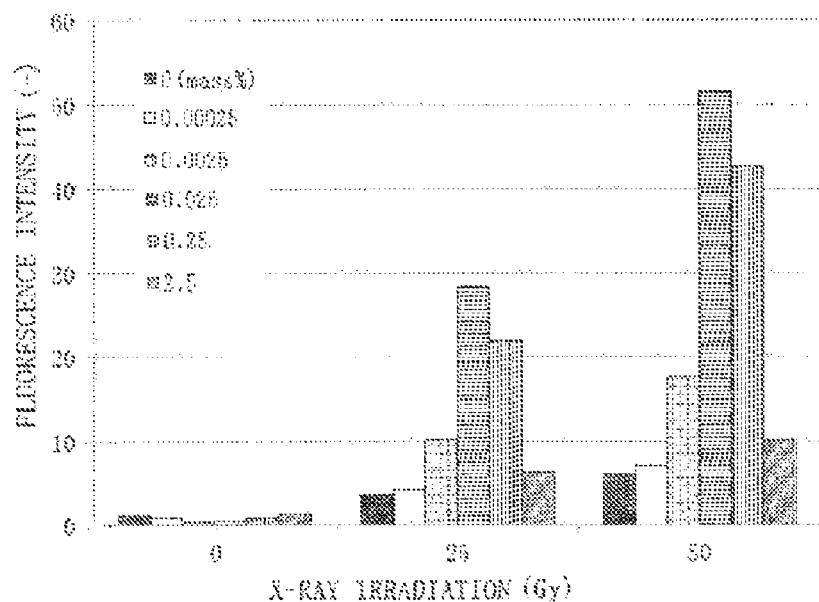
FIG. 1 A graph showing the amount of a hydroxyl radical generated in the case where a titanium peroxide-titanium dioxide substrate particle is irradiated with an X-ray (Experimental Example 1).

The present invention relates to a radiotherapeutic agent, including a composite particle obtained by binding a molecule that specifically recognizes a target to a substrate particle containing titanium peroxide, in which the radiotherapeutic agent exerts an action of attacking the target by a hydroxyl radical generated from titanium peroxide through radiation irradiation.

(Substrate Particle Containing Titanium Peroxide)

The substrate particle containing titanium peroxide in the present invention is a particle that contains titanium peroxide and is dispersible in a solution, and is also a particle that can generate reactive oxygen, in particular, a hydroxyl radical (.OH) in a solution through radiation irradiation. In this description, the substrate particle containing titanium peroxide is sometimes simply referred to as "substrate particle."

Titanium peroxide in the substrate particle has only to be present at least on a surface of the substrate particle. The substrate particle may contain a material other than titanium peroxide. The material other than titanium peroxide may be any material and is exemplified by oxide semiconductors such as titanium dioxide ($TiO_2$), zinc oxide (ZnO), tin oxide ($SnO_2$), tantalum oxide ($Ta_2O_3$), nickel oxide (NiO), iron oxide (FeO), chromium oxide (CrO, $Cr_2O_3$), and molybdenum oxide ($MoO_3$). The substrate particle is preferably a substrate particle containing titanium dioxide ($TiO_2$) in addition to titanium peroxide, and a substrate particle to be produced by a production method to be described later is preferably used. The substrate particle containing titanium dioxide in addition to titanium peroxide is hereinafter sometimes referred to as "titanium peroxide-titanium dioxide fine particle."

Further, the substrate particle of the present invention is desirably present as a dispersion liquid. A solvent for the dispersion liquid may be any solvent as long as the substrate particle is dispersible in the solvent, and is exemplified by distilled water. The average dispersed particle diameter of the substrate particle in the dispersion liquid is 1 nm or more to 200 nm or less, preferably 10 nm or more to 100 nm or less, more preferably 20 nm or more to 60 nm or less, under a physiological condition. This is because, when the average dispersed particle diameter of the substrate particle falls within the above-mentioned range, it is highly probable that the average dispersed particle diameter of a composite particle in the present invention also falls within a similar range, and the average dispersed particle diameter is a size enough to bind a molecule that specifically recognizes a target, which allows sufficient dispersion stability and fluidity to be ensured in an aqueous solution such as in blood stream of a mammal.

Herein, the dispersed particle diameter represents the size of the substrate particle in an aqueous solution, and includes the size of an aggregate in which crystals of the substrate particle aggregate with each other. The average dispersed particle diameter refers to an average value calculated by carrying out measurement by a dynamic light scattering method and analyzing the measured values by a cumulant method. Further, the phrase "under a physiological condition" as used herein refers to a condition of 25° C. and 1 atm in the presence of distilled water or a condition of 25° C. and 1 atm in the presence of phosphate buffered saline (having a composition of 137 mM NaCl, 8.1 mM $Na_2HPO_4$, 2.68 mM KCl, and 1.47 mM $KH_2PO_4$) (pH 7.4).

(Production Method for Substrate Particle Containing Titanium Peroxide)

The substrate particle containing titanium peroxide may be produced by any technique as long as the production of the particle having the above-mentioned properties is possible. The substrate particle containing titanium peroxide may be produced, for example, as described below. A neutralization reaction between titanium chloride or a hydrate thereof and a quaternary ammonium salt is carried out, the solution after the neutralization reaction is subjected to a hydrothermal treatment under a hydrothermal condition of 80 to 150° C., a hydrogen peroxide solution is added to the resultant dispersion liquid, and the mixture is washed by filtration. Thus, a dispersion liquid including the substrate particle containing titanium peroxide can be produced.

The titanium chloride is preferably titanium tetrachloride. The quaternary ammonium salt may be exemplified by tetramethylammonium hydroxide, tetramethylammonium carbonate, tetramethylammonium bicarbonate, choline, choline carbonate, and choline bicarbonate. Of those, tetramethylammonium hydroxide is preferred.

More specifically, the dispersion liquid including the substrate particle may be obtained by adding water (e.g., distilled water) and tetramethylammonium hydroxide (TMAH) to titanium tetrachloride ($TiCl_4$), subjecting the mixture to a heating treatment and a hydrothermal treatment at 125° C., and then adding a hydrogen peroxide solution, followed by washing by filtration with an ultrafiltration membrane.

(Molecule that Specifically Recognizes Target)

In the radiotherapeutic agent of the present invention, a molecule that specifically recognizes a particular target is bound to the substrate particle containing titanium peroxide. A particle including the substrate particle containing titanium peroxide and the molecule that specifically recognizes a particular target is referred to as composite particle. Both of the substrate particle containing titanium peroxide and the composite particle are each a nanoparticle, and the nanoparticle generally means a particle having a diameter of 1 nm or more to 200 nm or less.

The molecule that specifically recognizes a target has an action of accumulating the composite particle of the present invention in the target, and is, for example, a molecule that specifically binds to a molecule present in the target. The molecule may be any molecule such as a protein, a polypeptide, or DNA. The molecule is preferably a protein, and examples of the protein include an antibody, a ligand, and a receptor. Of those, an antibody is particularly preferred. For example, when the target is a tumor, it is recommended to use an antibody against a molecule specifically present in tumor cells. As the antibody against a molecule specifically present in tumor cells, specifically, there may be used an antibody against an epidermal growth factor receptor (EGFR), an antibody that recognizes a cancer antigen, or an antibody that recognizes a free antigen. Specific examples of the cancer antigen include an epidermal growth factor receptor (EGFR), an estrogen receptor (ER), and a progesterone receptor (PgR).

As a target functional group for the immobilization of the molecule that specifically recognizes a target, when the molecule is a simple protein, it is recommended to use each of an amino group and a thiol group, and when the molecule is a glycoprotein, it is recommended to use an aldehyde group of a sugar. For example, the immobilization utilizing an interaction between biotin and avidin can be achieved by preliminarily introducing biotin (or avidin) into a carboxyl group in a substrate particle modified with a water-soluble polymer and crosslinking a protein with avidin (or biotin).

(Polymer Coating Film)

The composite particle in the present invention preferably includes the substrate particle whose surface is at least partially coated with a polymer coating film. It is possible to easily bind the molecule that specifically recognizes a target to the surface of the substrate particle via the polymer coating film.

The polymer coating film in the present invention is preferably a coating film made of a water-soluble polymer. Examples of the water-soluble polymer include a hydrophilic cationic polymer and a hydrophilic anionic polymer. The substrate particle containing titanium peroxide is dispersible in a solution (in an aqueous solvent) in itself. However, for example, when the water-soluble polymer strongly binds to the surface of the substrate particle, the dispersion stability of the composite particle in solutions having a wide range of pHs including the vicinity of a neutral region can be enhanced. Further, even in a solution containing various components other than the composite particle like a medium or the like, the dispersion stability of the composite particle can be retained by virtue of the coating film made of the water-soluble polymer. In the case of the substrate particle containing titanium peroxide (preferably titanium peroxide-titanium dioxide fine particle), the dispersibility in water or various pH buffers each containing a salt becomes extremely satisfactory under a physiological condition and without addition of any other substance such as a dispersant, and stable dispersibility can be achieved over 24 hours or more.

A material for the polymer coating film in the present invention is desirably a water-soluble polymer having a carboxyl group or a water-soluble polymer as an amine. As the water-soluble polymer, there may be used any water-soluble polymer having a weight average molecular weight ranging from 1,000 or more to 100,000 or less. This allows a desired molecule that specifically recognizes a particular target to be immobilized on a carboxyl residue or an amino group and thus is useful. Examples of the polymer having a carboxyl group include carboxymethyl starch, carboxymethyl dextran, carboxymethyl cellulose, polycarboxylic acids, and copolymers each having a carboxyl group unit. Specifically, from the viewpoints of hydrolyzability and solubility of the water-soluble polymer, polycarboxylic acids such as polyacrylic acid and polymaleic acid, and copolymers of acrylic acid/maleic acid and acrylic acid/sulfonic acid-based monomers are more suitably used. Examples of the polymer as an amine include polyamino acids, polypeptides, polyamines, and copolymers each having an amine unit. Specifically, from the viewpoints of hydrolyzability and solubility of the water-soluble polymer, polyamines such as polyethylenimine, polyvinylamine, and polyallylamine are more suitably used. Alternatively, as the material for the polymer coating film, there may be used, for example, polyethylene glycol having a weight average molecular weight of 1,000 or more to 100,000 or less.

When the substrate particle containing titanium peroxide is modified with any of those water-soluble polymers, even after the immobilization of the molecule that specifically recognizes a particular target, an electrical repulsive force acts between particles owing to a functional group (a carboxyl group, an amino group, or a hydroxyl group) in the water-soluble polymer, and hence a state in which the particle is stably dispersed without causing any aggregation can be maintained in an aqueous dispersion medium having a pH of 3 to 9 over a long period of time. The dispersed particle diameter of the composite particle including the coating film made of the water-soluble polymer becomes constant at 1 nm or more to 200 nm or less under a physiological condition, and hence the composite particle shows excellent dispersion stability and fluidity in blood stream of a mammal, and the destruction of the target can be promoted by subjecting the composite particle which has reached the target to radiation irradiation.

(Formation of Polymer Coating Film)

The technique described in Patent Literature 2 may be employed as a technique for forming the polymer coating film on the substrate particle of the present invention. Specifically, the following technique may be employed. For example, in order to form a coating film made of a water-soluble polymer having a plurality of carboxyl groups on a substrate particle (preferably titanium peroxide-titanium dioxide fine particle), it is recommended to disperse the substrate particle and the water-soluble polymer having a plurality of carboxyl groups in dimethylformamide and subjecting the dispersion liquid to a hydrothermal reaction at 90 to 180° C. for 1 to 12 hours, thereby bonding the substrate particle to the water-soluble polymer via an ester bond. In this case, the ester bond between the substrate particle and the water-soluble polymer is an ester bond formed based on the phenomenon that titanium peroxide on the surface of the particle is hydrated with water in a reaction system to generate a hydroxyl group on the surface, and the hydroxyl group reacts with the carboxyl group in the water-soluble polymer. As a confirmation method for the ester bond, various analysis methods are applicable. For example, it is possible to confirm the ester bond based on the presence or absence of infrared absorption in an absorption band of the ester bond, i.e., around 1,700 to 1,800 $cm^{-1}$ by infrared spectroscopy.

The average dispersed particle diameter of the substrate particle having the polymer coating film in the dispersion liquid is substantially the same as that of the substrate particle having no polymer coating film, and is 1 nm or more to 200 nm or less, preferably 10 nm or more to 100 nm or less, more preferably 20 nm or more to 60 nm or less, under a physiological condition.

(Binding of Molecule that Specifically Recognizes Target to Substrate Particle)

It is possible to bind the molecule that specifically recognizes a target to the substrate particle itself directly or via a known linker. Alternatively, it is possible to bind the molecule via the polymer coating film that coats the substrate particle. The technique described in Patent Literature 2 may be employed as a technique for binding the molecule that specifically recognizes a target to the polymer coating film that coats the substrate particle. The polymer coating film is formed on the surface of the substrate particle, and hence a molecule having a specific binding ability to a molecule of interest can be immobilized on a carboxyl group or an amino group in the water-soluble polymer contained in the polymer coating film. For example, for the immobilization of the molecule having a specific binding ability on the polymer coating film on the surface of the substrate particle, an amino coupling method is carried out mainly through the use of the amino group or carboxyl group possessed by this molecule. For example, the amino group in the molecule that specifically recognizes a target can be bonded to the carboxyl group in the polymer coating film through the use of a water-soluble carbodiimide (EDC) and N-hydroxysuccinimide (NHS).

(Dispersion Liquid Including Composite Particle)

The present invention also encompasses a dispersion liquid including a composite particle. The optimum range of the surface potential of the composite particle of the present invention has only to be +20 mV or more. In general, the surface potential is more desirably +40 mV or more as a potential at which self-dispersion (state in which no particle precipitates) can be sufficiently achieved. Further, the dispersion liquid including the composite particle of the present invention desirably contains a salt, and the concentration of the salt is 1 M or less, preferably about 100 to 300 mM. Further, the concentration of the composite particle in the dispersion liquid has only to be, in terms of percent by weight (wt %), 20 wt % or less. More desirably, the concentration has only to be, in terms of percent by weight, 0.0001 to 10 wt %, preferably 0.001 to 5 wt %, more preferably 0.0025 to 2 wt %. It should be noted that the percent by weight (wt %) and the percent by mass (mass %) as used herein have the same meaning and are interchangeably used.

The dispersion liquid in the present invention may be provided as a homogeneous and stable dispersion liquid using any of water, various pH buffers, an infusion liquid, and physiological saline. The dispersion liquid including the composite particle of the present invention causes no aggregation even under a physiological condition near a neutral region, and hence is advantageous when administered to a living body.

(Radiotherapeutic Agent)

In the present invention, the radiotherapeutic agent means a medicament which may be used during radiotherapy. In the radiotherapeutic agent of the present invention, titanium peroxide contained in the substrate particle generates a hydroxyl radical through radiation irradiation, and the hydroxyl radical exerts an action of attacking a target. The radiotherapeutic agent according to the invention of the present application is a medicament that exerts a function of damaging a cell as a target through radiation irradiation.

The radiotherapeutic agent of the present invention may be formed into various formulation forms (e.g., a liquid formulation, a solid formulation, or a capsule). Examples of the formulation forms include an injection and an oral formulation (e.g., a tablet, a granule, a fine granule, a powder, a soft or hard capsule, a liquid formulation, an emulsion, a suspension, or a syrup). The radiotherapeutic agent according to the present invention may be manufactured in the various formulation forms in accordance with a method known per se. In the case of manufacturing the radiotherapeutic agent of the present invention, various additives may be added, if desired, depending on the kind of formulations. Examples of the additives include a stabilizer, an excipient, a lubricant, a disintegrant, a binder, a dissolving aid, a surfactant, a disintegration inhibitor, an antioxidant, a soothing agent, and a tonicity agent.

When the radiotherapeutic agent of the present invention is administered as an injection to a patient or the like, it is possible to appropriately select an administration route and administer the radiotherapeutic agent. For example, the radiotherapeutic agent may be administered directly or administered locally to a cancer-bearing tissue. Alternatively, the radiotherapeutic agent may be administered intravenously, intraarterially, subcutaneously, intramuscularly, or intraperitoneally.

As a radiation capable of enhancing a killing effect on a target when used in combination with the radiotherapeutic agent of the present invention, there is given, for example, an X-ray, a γ-ray, an electron beam, a proton beam, a helium line, a carbon ion beam, a neon ion beam, an argon ion beam, a silicon ion beam, a negative pion beam, a neutron beam, or a microwave. The radiation in the present invention is preferably an X-ray.

The frequency of administration of the radiotherapeutic agent of the present invention to a living body is not particularly limited and is, for example, one time to ten times. The timing of administration may be any timing of before or after a patient is subjected to radiation irradiation and at the same time as the irradiation, and is most preferably before radiation irradiation.

A known method may be employed as a method of irradiating a target with a radiation in radiotherapy, and is exemplified by a method involving carrying out fractionated irradiation (e.g., several minutes per day, a plurality of times over 1 to 2 months) directly. The initial energy of the radiation is generally about 100 to 500 MeV/n, which may be appropriately selected depending on, for example, the size, status or site, or local circumstances of a tumor in a patient or the like. Further, the irradiation dose of the radiation to a patient or the like is generally about 0.1 to 100 Gy, the irradiation rate of the radiation to a patient or the like is generally about 0.05 to 50 Gy/min, and energy to be transferred from the radiation to the target (linear energy transfer: LET) is generally about 50 to 70 keV/μm, all of which may be appropriately selected depending on, for example, the size, status or site, or local circumstances of a tumor in the patient or the like.

The target of the radiotherapeutic agent of the present invention may be any lesional tissue in a living body, and examples thereof include tumors including cancers, inflammatory tissues, and tissues infected with viruses. Examples of the tumors include lung cancer, ovary cancer, pancreatic cancer, stomach cancer, gallbladder cancer, kidney cancer, prostate cancer, breast cancer, esophageal cancer, liver cancer, oral cancer, colon cancer, large intestine cancer, uterus cancer, bile duct cancer, pancreatic islet cell cancer, adrenocortical cancer, bladder cancer, testis cancer, testicle tumor, thyroid cancer, skin cancer, malignant carcinoid tumor, malignant melanoma, osteosarcoma, soft tissue sarcoma, neuroblastoma, Wilms' tumor, retinoblastoma, melanoma, and glioma. The target of the the radiotherapeutic agent of the present invention is preferably pancreatic cancer or large intestine cancer.

The present invention also encompasses an antitumor agent, including the radiotherapeutic agent of the present invention. The antitumor agent of the present invention may be used in combination with chemotherapy using another antitumor agent, surgical therapy, or the like. Examples of the another antitumor agent include alkylating agents, various antimetabolites, and antitumor antibiotics.

EXAMPLES

Hereinafter, the present invention is more specifically described by way of examples and experimental examples in order to provide a thorough understanding of the present invention. However, it should be appreciated that the scope of the present invention is by no means limited by these examples and experimental examples.

Example 1

Production of Composite Particle (1) Production of Substrate Particle as Titanium Peroxide-Titanium Dioxide Fine Particle A substrate particle as a titanium peroxide-titanium dioxide fine particle was prepared as described below.

To 0.02 mol of titanium tetrachloride ($TiCl_4$) (manufactured by Wako Pure Chemical Industries, Ltd.) were added 10 ml of water and 30 ml of 25% (percent by weight) tetramethylammonium hydroxide (TMAH) (manufactured by TAMA CHEMICALS CO., LTD.), and the total volume was adjusted to 50 ml with water. The resultant was subjected to a heating treatment at 125° C. for 1 hour and cooled to room temperature. After that, 5 ml of a 30% (percent by weight) hydrogen peroxide solution were added. The resultant was washed five times by filtration with an ultrafiltration membrane (Amicon; manufactured by Millipore Corporation; molecular weight cut-off: 100 kDa) to produce a dispersion liquid of a substrate particle as a titanium peroxide-titanium dioxide fine particle (solvent: distilled water).

(2) Modification of Substrate Particle with Polymer

A surface of the substrate particle obtained in the section (1) was modified with polyacrylic acid as a polymer by the following technique.

First, DMF was added to polyacrylic acid (PAA) (weight average molecular weight: 5,000, Wako Pure Chemical Industries, Ltd.), followed by mixing, to produce a 100 mg/ml PAA solution. 1 ml of the 5% (percent by weight) dispersion liquid of the substrate particle produced in the above-mentioned section (1) and the 100 mg/ml PAA solution were subjected to ultrasonic irradiation with an ultrasonic generator for 30 minutes. 37.5 ml of DMF, 2 ml of the PAA solution, and 0.5 ml of the dispersion liquid of the substrate particle were mixed in this order. The mixture was subjected to an ultrasonic treatment until no precipitation was observed. The resultant was loaded into a sealed container made of Teflon (trademark) and subjected to a reaction at 150° C. for 5 hours. 10 ml each of the reaction liquid were dispensed into a 50 ml tube (Corning™), a two-fold volume (20 ml) of acetone was added, and the resultant mixed liquid was stirred and then left to stand still at room temperature for 1 hour. Centrifugation was carried out with a centrifugal machine at 4,000 rpm at 15° C. for 20 minutes, and the separated supernatant liquid was discarded by decantation. A two-fold volume (20 ml) of 99% (percent by weight) ethanol was added and the resultant mixed liquid was gently stirred and centrifuged with a centrifugal machine at 4,000 rpm for 10 minutes. The separated supernatant liquid was discarded by decantation. The residue was then suspended in distilled water so as to have a required concentration, to thereby produce a dispersion liquid of a PAA-modified substrate particle (hereinafter, sometimes referred to as "PAA-substrate particle").

It should be noted that the average dispersed particle diameter measured with a dynamic light scattering (DLS) method (Zetasizer Nano ZS, manufactured by Malvern) was about 58.4 nm. The average dispersed particle diameter was measured under the condition of 1 atm and 25° C. in the presence of distilled water.

(3) Binding of Anti-EGFR Antibody to PAA-Substrate Particle

To 125 μl of a 0.4 M water-soluble carbodiimide (EDC, Wako Pure Chemical Industries, Ltd.) solution were added 125 µl of a 0.1 M N-hydroxysuccinimide (NHS, Wako Pure Chemical Industries, Ltd.) solution. 250 µl of the mixed liquid were added to 500 µl of the 5% (percent by weight) PAA-substrate particle solution produced in the above-mentioned section (2) and the resultant mixed liquid was subjected to a reaction at room temperature for 1 hour while being gently stirred. To the mixed liquid were added 250 µl of a 0.02 M AB-NTA solution. After that, 500 µl of 0.015 M $Ni^{2+}$ were added and the resultant mixed liquid was stirred. To 50 µl of the mixed liquid were added 50 µl of a 0.02 M anti-EGFR antibody solution (an anti-EGFR antibody was prepared by the method described in Journal of Biochemistry, 46(6), 867-874) and the resultant mixed liquid was subjected to a reaction at 4° C. for 4 hours to overnight while being gently stirred. 1 ml of 0.1 M monoethanolamine was added and the resultant mixed liquid was subjected to a reaction at 4° C. for 30 minutes while being gently stirred, to thereby produce a composite particle including the anti-EGFR antibody bound to the PAA-substrate particle (hereinafter, sometimes referred to as "anti-EGFR antibody-PAA-substrate particle").

After the production of the composite particle, the composite particle was separated from the antibody that did not modify the substrate particle through the use of an ultrafiltration membrane (Amicon: manufactured by Millipore Corporation) having a molecular weight cut-off of 100 kDa. An HEPES buffer was added and the resultant mixed liquid was subjected to ultrafiltration three times.

Experimental Example 1

Confirmation of Radical Generation from Substrate Particle Through Radiation Irradiation Aminophenyl fluoroscein (APF) has substantially no fluorescence in a neutral aqueous solution. However, when APF reacts with a reactive oxygen species (in particular, .OH or $.O^{2-}$) having a strong activity, fluorescein as a strong fluorescent compound is generated. As a result, an increase in fluorescence intensity is observed. This reaction was utilized to confirm a change in the amount of a radical generated from the substrate particle (0, 0.00025, 0.0025, 0.025, 0.25, or 2.5 mass % (percent by mass)) obtained in the section (1) of Example 1 through radiation irradiation. The radiation irradiation was carried out with a high-energy X-ray irradiation apparatus for clinical use Linac: Mitsubishi EXL-15DP (hereinafter, also referred to as "X-ray irradiation apparatus for clinical use") or a Spring-8 apparatus at an irradiation dose with a uniform gray (Gy) number (0 to 100 Gy) in accordance with the instructions of the apparatus. Further, as a positive control, the substrate particle was subjected to ultraviolet ray irradiation to confirm a change in the amount of a radical generated. The ultraviolet ray irradiation was carried out through the use of DNA-FIX manufactured by ATTO with a uniform irradiation Joule amount (0 to 16 $J/cm^2$). In addition, as a negative control, radiation irradiation was carried out through the use of a PAA-modified titanium dioxide fine particle (dispersed in distilled water). It should be noted that the titanium dioxide fine particle used was a product name "STS01" (manufactured by ISHIHARA SANGYO KAISHA, LTD.).

Figure 2:
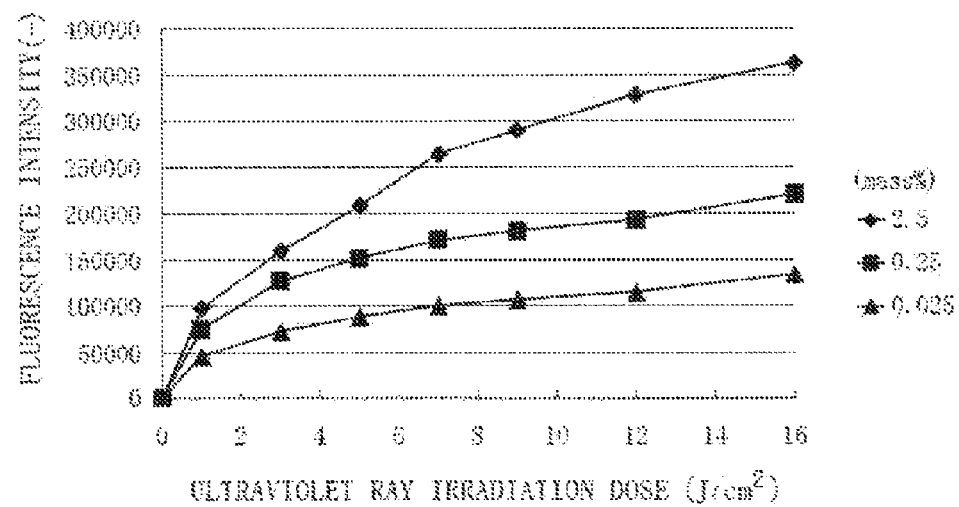
FIG. 2 A graph showing the amount of a hydroxyl radical generated in the case where a titanium peroxide-titanium dioxide substrate particle is irradiated with an ultraviolet ray (Experimental Example 1).

FIGS. 1 to 4 show the results. FIG. 1 shows the results of irradiation of the substrate particle with an X-ray through the use of the X-ray irradiation apparatus for clinical use, and FIG. 2 shows the results of irradiation of the substrate particle with an ultraviolet ray. FIG. 3 each show the results of irradiation of the substrate particle containing titanium peroxide with an X-ray through the use of the X-ray irradiation apparatus for clinical use or Spring-8, and FIG. 4 each show the results of irradiation of the PAA-modified titanium dioxide fine particle with an X-ray through the use of the X-ray irradiation apparatus for clinical use or Spring-8. The results confirmed that the substrate particle containing titanium peroxide generated a radical through radiation irradiation. The results revealed that the amount of the radical generated from the substrate particle containing titanium peroxide was larger than the amount of the radical generated from the titanium dioxide fine particle. The results also revealed that as the concentration of the substrate particle containing titanium peroxide became higher, the amount of the radical generated increased, until the concentration reached a given concentration.

Experimental Example 2

Confirmation of Cytotoxic Effect of Composite Particle

Investigations were made on cancer cell specificity of the composite particle produced in Example 1 and cancer cell-killing/damaging effects of the composite particle. In Experimental Example 1, it was confirmed that the substrate particle containing titanium peroxide generated a radical through radiation irradiation. Hence, in this experimental example, for the sake of convenience, an experiment was carried out through the use of ultraviolet ray irradiation in place of radiation irradiation.

2 ml each of a cancer cell (Hela cell) suspension were added to a 3.5 cm dish at $2 \times 10^5$ cells/dish. A DMEM medium (manufactured by NACALAI TESQUE, INC.) was used as a medium. Incubation was carried out in 5% $CO_2$ at 37° C. for 24 hours. The medium was discarded, 2 ml of a fresh medium were added, and 0.15 ml of a 1% (percent by weight) composite particle (anti-EGFR antibody-PAA-substrate particle) was added. Next, ultraviolet ray irradiation (condition: 3.0 $J/cm^2$) was carried out. As controls, cells in a medium only, a medium having added thereto a red fluorescent protein (RFP), a medium having added thereto an anti-EGFR antibody only, a medium having added thereto a PAA-substrate particle, and a medium having added thereto an RFP-modified PAA-substrate particle (hereinafter, also referred to as "RFP-PAA-substrate particle") were also subjected to ultraviolet ray irradiation. After that, ethidium homodimer 1 (EthD-1) and calcein were added, and the cells were observed with a fluorescent microscope. Viable cells show green fluorescence and killed cells show red fluorescence.

Figure 6:
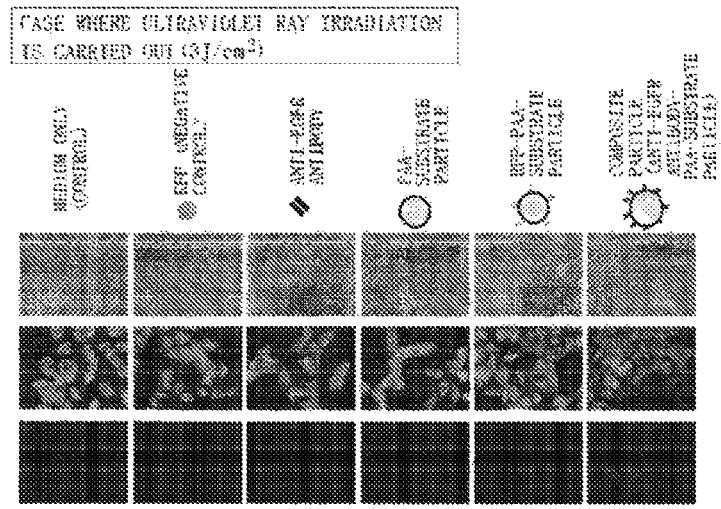
FIG. 6 Photographs each showing cytotoxicity in the case where the composite particle of the present invention is irradiated with an ultraviolet ray (Experimental Example 2).

FIG. 5 are photographs of the cells in the case where no ultraviolet ray irradiation was carried out, and FIG. 6 are photographs of the cells in the case where ultraviolet ray irradiation was carried out. The photographs at the top of each of FIG. 5 and FIG. 6 are transmitted light images, the photographs in the middle are green fluorescent images (viable cells), and the photographs at the bottom are red fluorescent images (dead cells). In the case where the composite particle of the present invention was subjected to ultraviolet ray irradiation, killed cells were clearly observed, indicating that the composite particle exerted cytotoxicity. It should be noted that killed cells were also observed in the case where the anti-EFGR antibody was absent, but a larger number of cells were killed in the case of the composite particle with the anti-EGFR antibody, suggesting that accumulation property in cancer cells was important for the exertion of specific cytotoxicity.

Experimental Example 3

Confirmation of Cytotoxic Effect of Composite Particle

Investigations were made on cancer cell specificity of the composite particle produced in Example 1 and cancer cell-killing/damaging effects of the composite particle. In this experimental example, radiation irradiation was carried out, and the effects were confirmed.

Cancer cells (MIA PaCa-2 cells: human pancreatic adenocarcinoma or HCTp53+/+ cells: human large intestine cancer (both were obtained from ATCC)) were added to a 96-well plate at $1\times10^3$ cells/well. A RPMI medium (manufactured by NACALAI TESQUE, INC.) was used as a medium in each case. It is known that EGFR is expressed in both the MIA PaCa-2 cells and the HCTp53+/+ cells. Incubation was carried out in 5% $CO_2$ at 37° C. for 24 hours. The medium was discarded, 2 ml of a fresh medium were added, and 0.15 ml of a 1.6% (percent by weight) composite particle (anti-EGFR antibody-PAA-substrate particle) was added. Next, X-ray irradiation (0, 5 Gy) was carried out. The X-ray irradiation was carried out with the same high-energy X-ray irradiation apparatus for clinical use as in Experimental Example 1 Linac: Mitsubishi EXL-15DP (150 kVp, 5 mA, 1.0 Al Filter). As controls, cells in a medium only and a medium having added thereto a 1.6% (percent by weight) PAA-substrate particle were subjected to X-ray irradiation. A day on which the X-ray irradiation was carried out was defined as Day 0, and the number of viable cells was measured on Day 7 for the MIA PaCa-2 cells and on Day 12 for the HCTp53+/+ cells. The number of viable cells was measured by adding WST-8 (Cell Counting Kit-8, DOJINDO LABORATORIES) and incubating the mixture for 3 hours, followed by measurement of an absorbance at 490 nm. A cell viability was calculated as a ratio relative to the number of cells in the case of 0 Gy.

Figure 7:
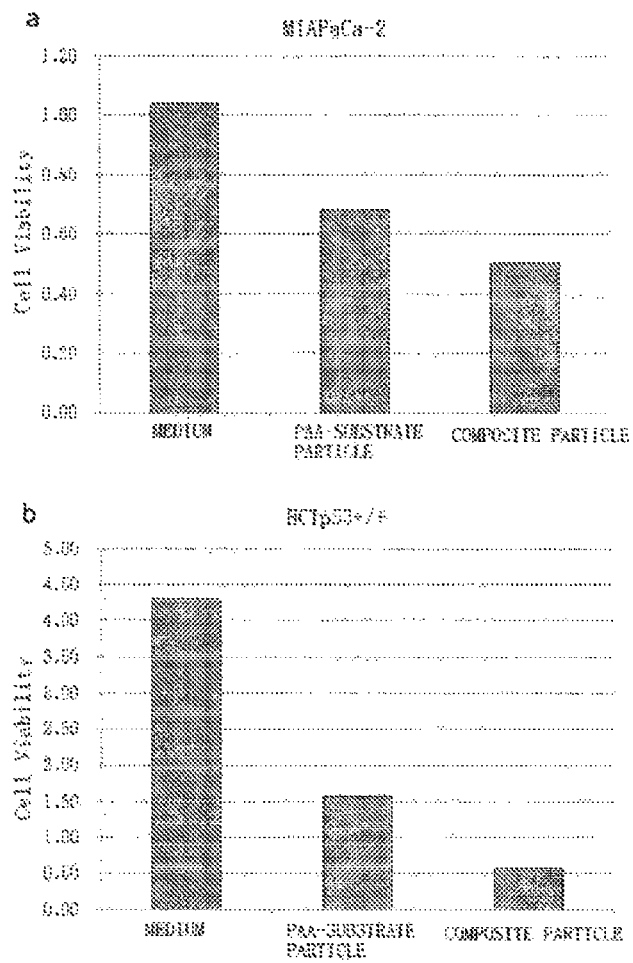
FIGS. 7a and 7b Photographs each showing cytotoxicity in the case where the composite particle of the present invention is irradiated with an X-ray or not (Experimental Example 3).

FIGS. 7a and 7b show the results. FIG. 7a shows the results of the MIA PaCa-2 cells, and FIG. 7b shows the results of the HCTp53+/+ cells. The number of the cells decreased in each of the case of adding the PAA-substrate particle and the case of adding the composite particle containing the anti-EGFR antibody, as compared to the control including the medium only, confirming that a cytotoxic effect was exhibited through the irradiation of the substrate particle with an X-ray. In both of the cells, the number of the cells decreased in the case of adding the composite particle containing the antibody as compared to the case of adding the PAA-substrate particle, from which it was estimated that the composite particle was accumulated in cancer cells to enhance a cytotoxic effect through the inclusion of the anti-EGFR antibody.

INDUSTRIAL APPLICABILITY

According to the radiotherapeutic agent of the present invention, the composite particle is accumulated in a target through a molecule that specifically recognizes the target, and titanium peroxide generates a hydroxyl radical through radiation irradiation, which allows the target to be damaged. The use of the radiotherapeutic agent of the present invention allows the target to be effectively damaged even at a small radiation dose. When the radiotherapeutic agent of the present invention is used to carry out oncotherapy or the like, side effects of a radiation on a normal tissue other than a tumor can be reduced, the burden of radiotherapy on a patient is reduced, and the usefulness of radiotherapy is increased. The utilization of the radiotherapeutic agent of the present invention eliminates a need for irradiating a tumor or the like present in a deep portion with a strong radiation. This is expected to allow therapies for cancer to be carried out while keeping the QOL of a patient.

The invention claimed is:

1. A radiotherapeutic agent, comprising a composite particle, which is obtained by binding a molecule that specifically recognizes a target to a substrate particle comprising titanium peroxide, and which generates reactive oxygen that damages the target through X-ray irradiation.

2. A radiotherapeutic agent according to claim 1, wherein the reactive oxygen comprises a hydroxyl radical.

3. A radiotherapeutic agent according to claim 1, wherein the titanium peroxide in the substrate particle is mainly distributed on a surface of the substrate particle.

4. A radiotherapeutic agent according to claim 1, wherein the substrate particle further comprises titanium dioxide.

5. A radiotherapeutic agent according to claim 1, wherein the substrate particle has an average dispersed particle diameter of 1 nm or more to 200 nm or less.

6. A radiotherapeutic agent according to claim 1, wherein the molecule that specifically recognizes a target comprises an antibody.

7. A radiotherapeutic agent according to claim 1, wherein the composite particle comprises the substrate particle whose surface is at least partially coated with a polymer coating film, and is obtained by binding the molecule that specifically recognizes a target to the substrate particle via the polymer coating film.

8. A dispersion liquid, comprising a composite particle self-dispersed in water, a pH buffer, an infusion liquid, or physiological saline, wherein the composite particle comprises a composite particle, which is obtained by binding a molecule that specifically recognizes a target to a substrate particle comprising titanium peroxide, and which generates reactive oxygen that damages the target through X-ray irradiation.

9. A dispersion liquid according to claim 8, wherein the composite particle has a surface potential of +20 mV or more.

10. A radiotherapeutic agent, comprising the dispersion liquid according to claim 8.

11. An antitumor agent, comprising the radiotherapeutic agent according to claim 1, wherein the molecule that specifically recognizes a target comprises an antibody capable of specifically recognizing a tumor cell.

* * * * *